(12) United States Patent
Abe

(10) Patent No.: US 6,848,157 B2
(45) Date of Patent: Feb. 1, 2005

(54) DISPOSABLE SYRINGE DEVICE AUXILIARY UNIT FOR PREVENTING IATROGENIC INFECTION THROUGH NEEDLE

(76) Inventor: Koichiro Abe, 18 Daikyocho, Shinjuku-ku, Tokyo (JP)

( * ) Notice: Subject to any disclaimer, the term of this patent is extended or adjusted under 35 U.S.C. 154(b) by 0 days.

(21) Appl. No.: 10/006,717

(22) Filed: Dec. 10, 2001

(65) Prior Publication Data
US 2002/0195362 A1 Dec. 26, 2002

(30) Foreign Application Priority Data
Jun. 22, 2001 (JP) ........................................ 2001-189973

(51) Int. Cl.[7] ............................ A61M 5/00; A61M 5/32; B23P 19/00; A61J 1/00; A44B 9/12
(52) U.S. Cl. ........................ 29/240; 215/366; 205/366; 29/426.5; 604/192; 604/263; 604/187
(58) Field of Search ................................ 29/426.5, 240; 206/366, 365, 370; 215/366; 604/92–198, 263, 11, 411, 403, 414, 200, 232, 502

(56) References Cited

U.S. PATENT DOCUMENTS

| 4,836,373 A | * | 6/1989 | Goldman | 206/366 |
| 4,979,945 A | * | 12/1990 | Wade et al. | 604/192 |
| 5,067,223 A | * | 11/1991 | Bruno | 29/426.5 |
| 5,084,028 A | * | 1/1992 | Kennedy et al. | 604/192 |
| 5,183,156 A | * | 2/1993 | Bruno | 206/366 |
| 5,356,384 A | * | 10/1994 | Haber | 604/110 |
| 5,469,964 A | * | 11/1995 | Bailey | 206/364 |

FOREIGN PATENT DOCUMENTS

JP    2000-316919    11/2000

* cited by examiner

Primary Examiner—Nicholas D. Lucchesi
Assistant Examiner—Roz Maiorino
(74) Attorney, Agent, or Firm—Armstrong, Kratz, Quintos, Hanson & Brooks, LLP

(57) ABSTRACT

A disposable syringe device auxiliary unit of the present invention for preventing iatrogenic infection through a needle includes a cap holding section for disposing and holding therein a cap which covers, when a medical treatment is performed, a needle positioned at the extreme end of a syringe barrel constituting a disposable syringe device; and a needle separating section for separating the needle, which is covered with the cap and fitted on an end of the syringe barrel, therefrom.

10 Claims, 9 Drawing Sheets

DISPOSABLE SYRINGE DEVICE AUXILIARY UNIT FOR PREVENTING IATROGENIC INFECTION THROUGH NEEDLE

This application claims benefit of Japanese Application No. 2001-189973 filed on Jun. 22, 2001, the contents of which are incorporated by this reference.

BACKGROUND OF THE INVENTION

1. Field of the Invention

The present invention relates to a disposable syringe device auxiliary unit for enabling a cap to be attached to a needle or enabling the needle to be removed from a disposable syringe device with one hand.

2. Description of the Related Art

Recently, disposable syringe devices that are discarded when they are used once, that is, so-called disposable syringe devices are widely used to prevent iatrogenic infection through syringe devices. The disposable syringe device is composed of a sterilized disposable syringe and a sterilized needle mounted thereon. The needle is covered with a sterilized cap.

Therefore, when chemicals are injected into or blood is collected from a patient using the disposable syringe device, the cap is detached, and the exposed needle is stuck under or in the skin, in the muscle or in the blood pipe of the patient.

One of the most serious problems in medical disasters, which happen to doctors, nurses, and medical practicians in a medical site, is a so-called accidental needle stick in which a used needle is stuck in a hand or a finger of them. The accidental needle stick happens when a person sticks the extreme end of an exposed needle in himself or herself or in other person by mistake after he or she collects blood from or injects chemicals into a patient. In addition to the above, however, there is also a possibility that the accidental needle stick happens when a cap is attached to the needle again.

The accidental needle stick, which happens when the cap is attached to the needle again, is caused at the time the needle of a disposable syringe device, which is held with one hand, is inserted into a cap held with the other hand.

Further, in an operation in which a disposable syringe device may be used repeatedly, there is a possibility that the accidental needle stick happens when a disposable syringe device used once is left with the needle thereof exposed because a cap is lost or when a needle is repeatedly separated from and mounted on again a syringe barrel to draw chemicals into the syringe barrel.

Further, the accidental needle stick also happens when a person comes in touch with a needle without a cap by mistake when used disposable syringe devices are discarded as medical wastes, and when needles are discarded in the state that they are separated from syringe barrels.

SUMMARY OF THE INVENTION

An object of the present invention is to provide a disposable syringe device auxiliary unit for preventing a cap, which is detached from a disposable syringe device just before it is used, from being lost.

Another object of the present invention is to provide a disposable syringe device auxiliary unit for enabling a cap to be reliably and easily attached again to the needle of a disposable syringe device after the device is used while preventing a hand and a finger from being stuck with the needle by mistake.

Still another object of the present invention is to provide a disposable syringe device auxiliary unit for preventing the hand and finger of a medical practician from being stuck with the needle of a disposable syringe device by mistake when he or she separates the needle from a syringe barrel.

To describe briefly, the disposable syringe device auxiliary unit of the present invention includes a cap holding section, in which a cap covering a needle positioned at the extreme end of a syringe barrel constituting a disposable syringe device, is disposed and held in a medical treatment; and a needle separating section for separating the needle, which is covered with the cap and fitted on an end of the syringe barrel, therefrom. With this arrangement, it can be prevented to lose the cap covering the needle as well as the occurrence of a medical disaster caused by an accidental needle stick can be prevented because the cap is attached to the needle and the needle is separated from the syringe barrel with one hand.

The above and other objects, features and advantages of the invention will become more clearly understood from the following description referring to the accompanying drawings.

BRIEF DESCRIPTION OF THE DRAWINGS

FIG. 1A to FIG. 6C show a first embodiment of the present invention, wherein:

FIG. 1A is a view explaining a disposable syringe device of a type in which the inner peripheral surface of the joint section of a needle is fitted on the projection of an outer barrel;

FIG. 2 is a view explaining a disposable syringe device auxiliary unit;

FIG. 3 is a view explaining a needle accommodation box to which the disposable syringe device auxiliary unit is attached;

FIG. 6C is a view showing a state in which the needle to which the cap is attached again is separated from the projection;

FIG. 8 to FIG. 11 are views explaining a second embodiment of the present invention, wherein:

FIG. 8 is a view explaining a needle separation auxiliary unit;

FIG. 10 is a view explaining a needle accommodation body with which the needle separation auxiliary unit and the cap holding auxiliary unit are integrated;

FIG. 11 is a view explaining the operation of the needle separation auxiliary unit and the cap holding auxiliary unit that are integrated with the needle accommodation box.

DETAILED DESCRIPTION OF THE PREFERRED EMBODIMENTS

A first embodiment of the present invention will be described below with reference to FIGS. 1 to 6.

Figure 1A:
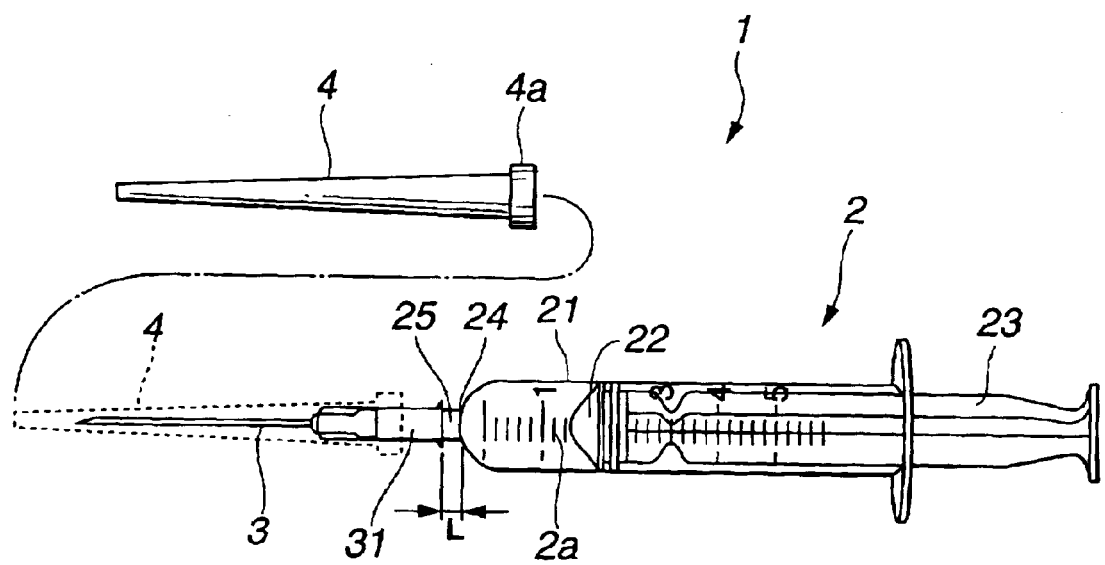

A disposable type syringe device (hereinafter, referred to simply as a "disposable syringe device") will be described below with reference to FIG. 1A.

As shown in the figure, a disposable syringe device 1 is composed of a disposable syringe 2 acting as a syringe barrel, a needle 3 detachably attached to the disposable syringe 2, and a cylindrical cap 4 for preventing the needle 3 from being left in an exposed state.

The cap 4 covers the needle 3 as shown by a dotted line. With this arrangement, the needle 3 is prevented from being left in the exposed state. The disposable syringe 2, the needle 3, and the cap 4 have been sterilized.

The disposable syringe 2 is composed of an outer barrel 21 and an inner barrel 23 that is slidable with respect to the inner hole of the outer barrel 21. A scale 2a is formed on the outer surface of the outer barrel 21 to measure an amount of chemicals, and the like. A stopper 22 is disposed to the extreme end of the inner barrel 23. Further, an approximately conical projection 25 projects from an extreme end surface 24 of the outer barrel 21.

An approximately conical joint section 31 is disposed to the base end portion of the needle 3. The joint section 31 has an inner peripheral surface, which is fitted on the outer peripheral surface of the projection 25 and integrated with the disposable syringe 2, and an outer peripheral surface on which the inner peripheral surface of the cap 4 on the opening side thereof is fitted.

That is, the disposable syringe device 1 of the first embodiment is a type in which the needle 3 and the disposable syringe 2 are disposed in an integrated state in such a manner that the inner peripheral surface of the joint section 31 is fitted on the projection 25 of the outer barrel 21. Then, the needle 3 can be removed from the projection 25 of the outer barrel 21 by releasing the fitting state between the joint section 31 and the projection 25.

When the needle 3 is integrated with the disposable syringe 2, a gap having a size "L" is formed between the base end surface of the joint section 31 and the extreme end surface 24 of the outer barrel 21.

The cap 4 is disposed integrally with the needle 3. The cap 4 is integrated with the needle 3 by fitting and disposing a collar section 4a of the cap 4, which is formed in the base end portion thereof, on the outer peripheral surface of the joint section 31 of the needle 3.

Figure 1B:
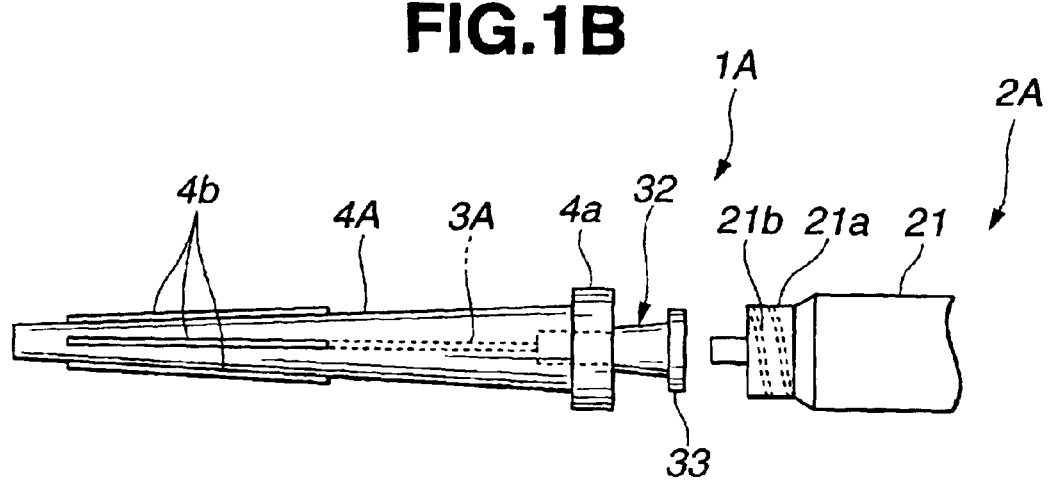
FIG. 1B is a view explaining a locking type disposable syringe device.

Note that the disposable syringe device 1 is not limited to the type in which the needle 3 is integrated with the projection 25 by being fitted thereon and may be arranged as a locking type disposable syringe device 1A as shown in FIG. 1B.

In the locking type disposable syringe device 1A, a spiral projection 21b is formed on the inner peripheral surface of an extreme end 21a of the outer barrel 21. In contrast, a guide projection 33, which moves along the spiral projection 21b, is formed to a base end section 32 of a needle 3A.

Accordingly, in the needle 3A, when the guide projection 33 is moved inward along the spiral projection 21b, the needle 3A is locked and fixed to the extreme end 21a of a disposable syringe 2A as if it is in a threaded state. When the guide projection 33 is moved to the outside which is in a direction opposite that when it is fixed, in the same way for releasing a threaded state, the needle 3A can be released from the locked and fixed state.

A plurality of line-shaped slender projections 4b, which project in an axial direction, are formed on the outer peripheral surface of a cap 4A used in the locking type disposable syringe device 1A.

The arrangement and the operation of the disposable syringe device auxiliary unit of the first embodiment will be described with reference to FIGS. 2 to 6.

Figure 2:
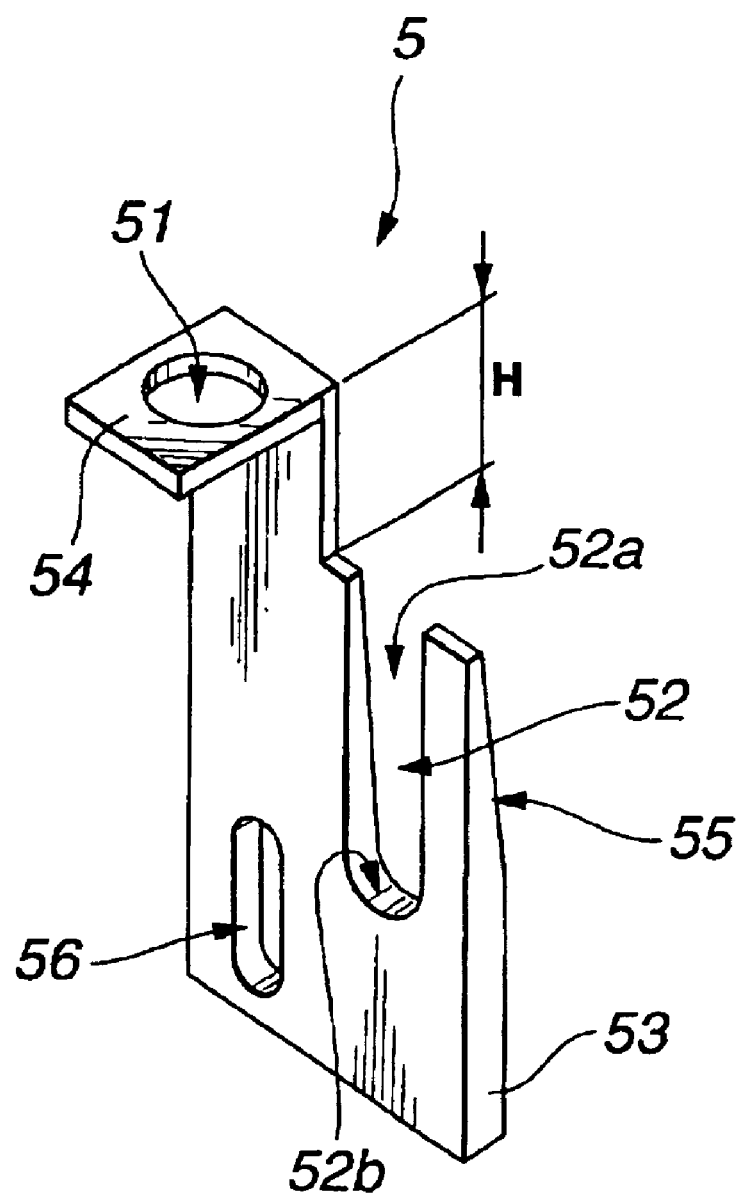
Figure 3:
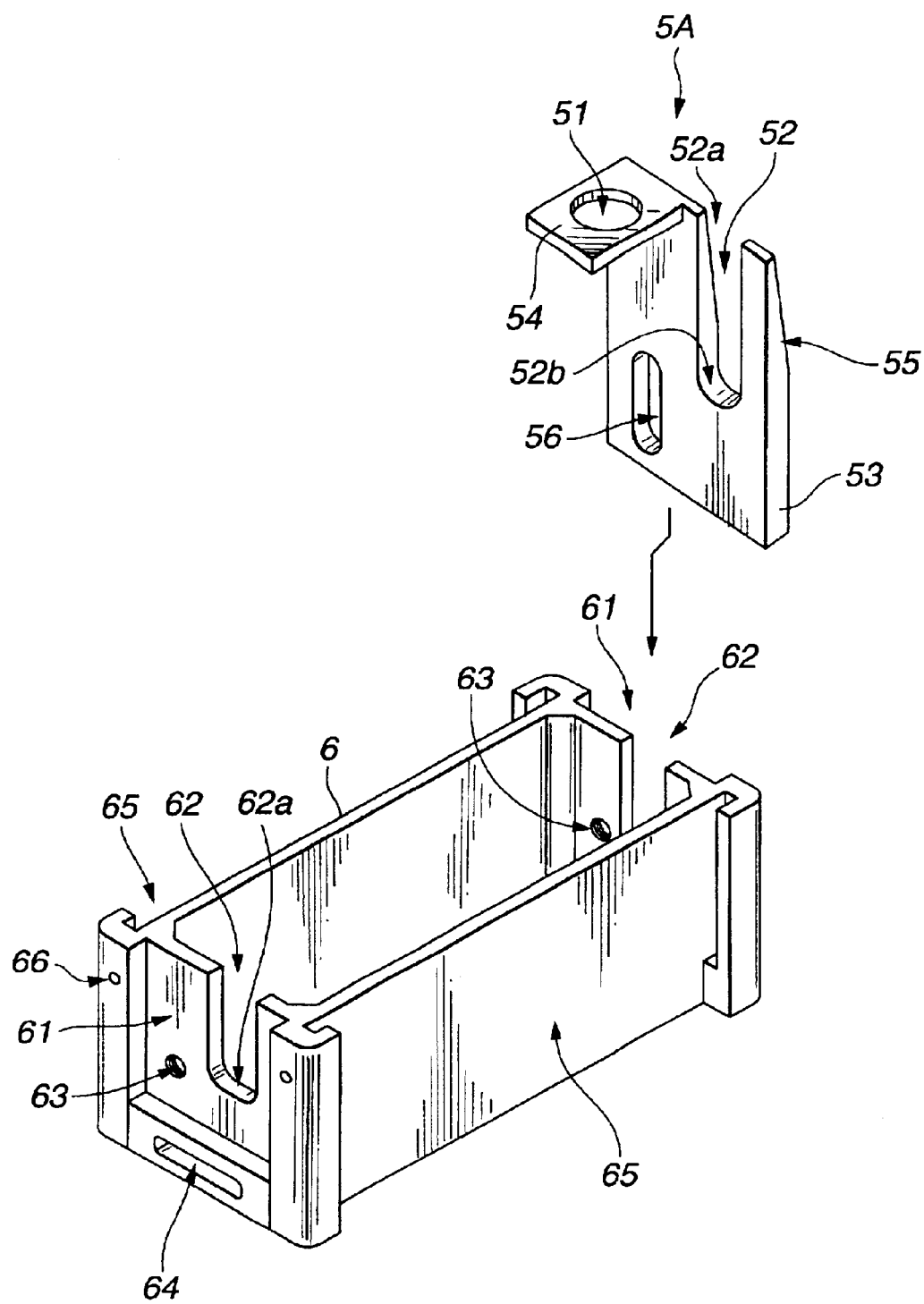

As shown in FIGS. 2 and 3, the disposable syringe device auxiliary unit of the first embodiment (hereinafter, abbreviated as a "syringe auxiliary unit") 5 is formed of a sheet member 53. A hole section 51 and a separation/guide groove 52 are formed in the sheet member 53 integrally therewith. The hole section 51 acts as a cap holding section where the cap 4 is disposed and held, and the separation/guide groove 52 acts as a needle separating section for separating the needle 3 from the disposable syringe 2.

The hole section 51 of the syringe auxiliary unit 5 is formed through a bent section 54 which is formed by bending the sheet member 53 at a predetermined portion at an approximately right angle. The extreme end of the cap 4 is inserted into the hole section 51 from the upper surface side thereof.

The separation/guide groove 52 is formed in a width which permits the projection 25 to be disposed therein in a loosely fitting state and in a predetermined depth. A slanting surface 55, which separates the joint section 31 of the needle 3 from the projection 25 of the disposable syringe 2, is formed on the surface of the sheet member 53 which is opposite to the surface thereof where the bent section 54 is formed.

The slanting surface 55 is formed such that the thickness of the sheet member 53 is continuously made thicker from an opening 52a side of the separation/guide groove 52 to a predetermined position somewhat lower than a bottom 52b of the separation/guide groove 52.

Specifically, the slanting section 55 has a thickness which is smaller than the above size "L" on the opening side thereof and a thickness which causes the joint section 31 fitted on the projection 25 to be separated therefrom at a mid-portion thereof. Then, the thickness of the sheet member 53 is set larger than the thickness which causes the joint section 31 to be separated from the projection 25.

Accordingly, when the portion of the interval, which has the size "L", of the disposable syringe 2 to which the needle 3 is joined, is disposed in the separation/guide groove 52 and moved from the opening 52a side to the bottom 52b side, the locked and fixed state between the joint section 31 and the projection 25 is changed to a separated state.

Note that while the cap 4 roughly has three kinds of size, a cap having a different size can be handled by appropriately setting the distance "H" from the end surface of the sheet member 53 on the opening side thereof to the bent section 54 as shown in FIG. 2.

Further, reference numeral 56 denotes a slot for adjusting the position of the syringe auxiliary unit 5 where it is mounted. The position, where the syringe auxiliary unit 5 is mounted on a needle accommodation box 6 which will be described later, can be changed by moving it along the slot 56.

With the above arrangement, the cap 4 can be disposed in an upright state even if it has a different length. That is, the size "H" and the slot 56 act as a cap length adjustment section.

As shown in FIG. 3, a syringe barrel and needle holding/separating apparatus can be arranged by mounting a syringe auxiliary unit 5A arranged as described above on the needle accommodation box 6. The needle accommodation box 6 is formed in an approximately box shape and composed of, for example, stainless steel. A pair of auxiliary unit mounting sections 61 are disposed along the short sides of the needle accommodation box 6. The syringe auxiliary unit 5A is mounted on any one of the auxiliary unit mounting sections 61 by a fixing screw 59 shown in FIG. 4C.

It should be noted that, in the syringe auxiliary unit 5A of the first embodiment, the size "H" is set to H=0. Further, reference numeral 65 denotes a pair of second auxiliary unit mounting sections disposed along the long sides of the needle accommodation box 6.

An escape groove 62 is formed to the position, which corresponds to the separation/guide groove 52 of syringe auxiliary unit 5A, of each of the auxiliary unit mounting sections 61. The escape groove 62 has a width larger than the width of the separation/guide groove 52 by a predetermined size. A bottom 62a of the escape groove 62 is positioned nearer to a bottom 6a of the needle accommodation box 6 than the bottom 52b of the separation/guide groove 52.

Further, a first female screw section 63, into which the fixing screw passing through the slot 56 is threaded, and a mounting/fixing hole 64 are formed in the auxiliary unit mounting sections 61. When the needle accommodation box 6 is fixed to, for example, a visiting car, a fixture (not shown), on which the needle accommodation box 6 is to be mounted, is disposed through a mounting/fixing hole 64.

Note that reference numeral 66 denotes second female screw sections with which fixing screws are threaded to hold and fix an auxiliary unit which is disposed to any one of the second auxiliary unit mounting sections 65.

Figure 4A:
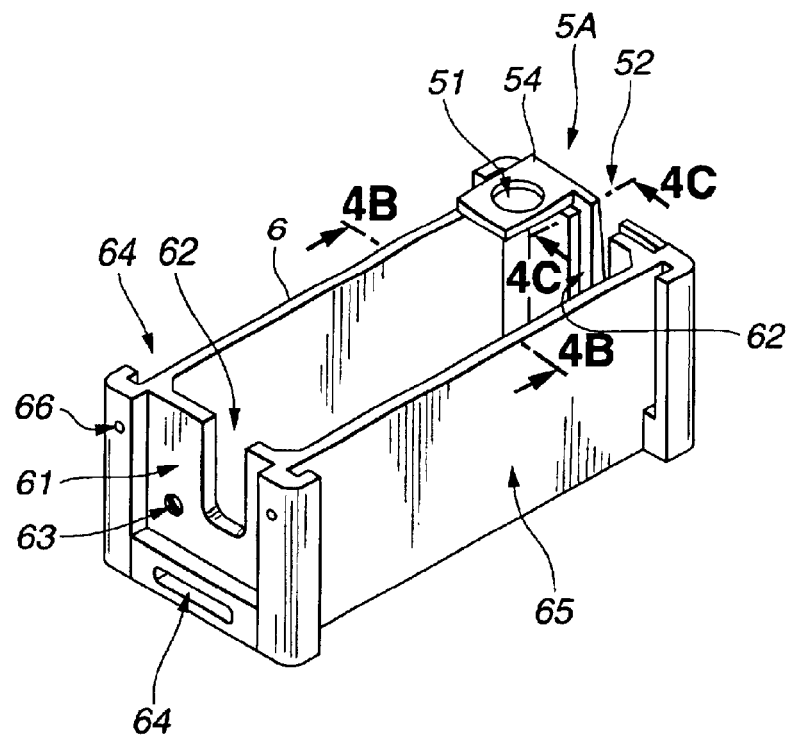
FIG. 4A is a perspective view of the needle accommodation box integrated with the disposable syringe device auxiliary unit.
Figure 4B:
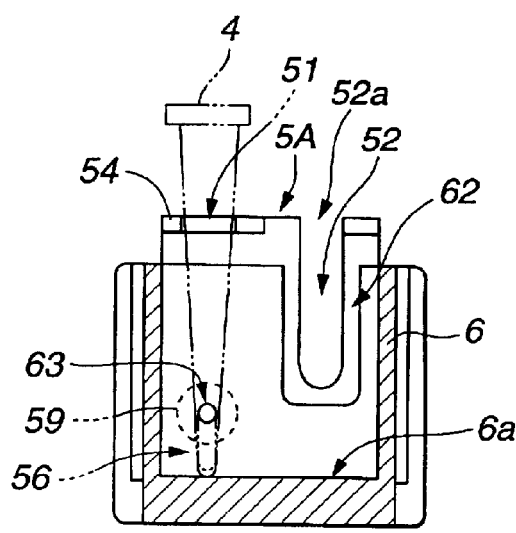
FIG. 4B is a sectional view of the needle accommodation box taken along the line 4B—4B of FIG. 4A.
Figure 4C:
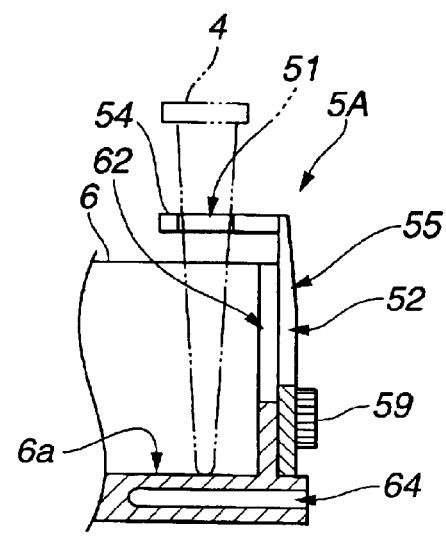
FIG. 4C is a sectional view of the needle accommodation box taken along the line 4C—4C of FIG. 4A.

As shown in FIG. 4A, the syringe auxiliary unit 5A is disposed to one of the auxiliary unit mounting sections 61 of the needle accommodation box 6. Then, the fixing screw 59 is threaded into the first female screw section 63 through the slot 56 so as to integrate the syringe auxiliary unit 5A with the needle accommodation box 6. At this time, the height of the hole 51 from the bottom 6a is adjusted by moving the syringe auxiliary unit 5A with respect to the slot 56 so that the cap 4 stands upright with the extreme end thereof in contact with the bottom 6a as shown by a two-dot-and-dash line in FIGS. 4B and 4C.

Then, the needle accommodation box 6, which is integrated with the syringe auxiliary unit 5A, is fixed to the visiting car (not shown) integrally therewith at a predetermined position thereof through the fixture (not shown), which carries medical appliances, for example, disposable syringe devices, various kinds of chemicals, gauze, absorbent cottons, waste bags, etc., in order to go to a doctor's round visit.

The operation of the syringe auxiliary unit 5A integrated with the needle accommodation box 6 will be described below.

Figure 5A:
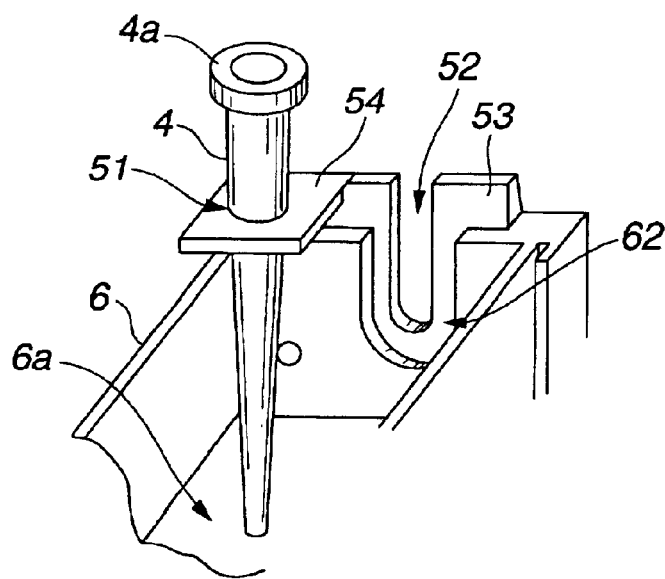
FIG. 5A is a view showing a state in which a cap stands in a hole.

When it is necessary to inject chemicals to a patient during the doctor's round visit, first, a disposable syringe device 1 carried by the visiting car is taken out. Then, the cap 4 of the disposable syringe device 1 is detached. Then, the extreme end side of the cap 4 is inserted into the hole 51 of the syringe auxiliary unit 5A from thereabove. With this operation, as shown in FIG. 5A, the extreme end surface of the cap 4 comes into contact with the bottom 6a of the needle accommodation box 6 as well as the cap 4 is held in the hole 51 in a state that a mid-portion of the slanting surface of the cap 4 is forcibly inserted into the hole 51. When the cap 4 is held in the hole 51, it stands approximately upright.

Figure 5B:
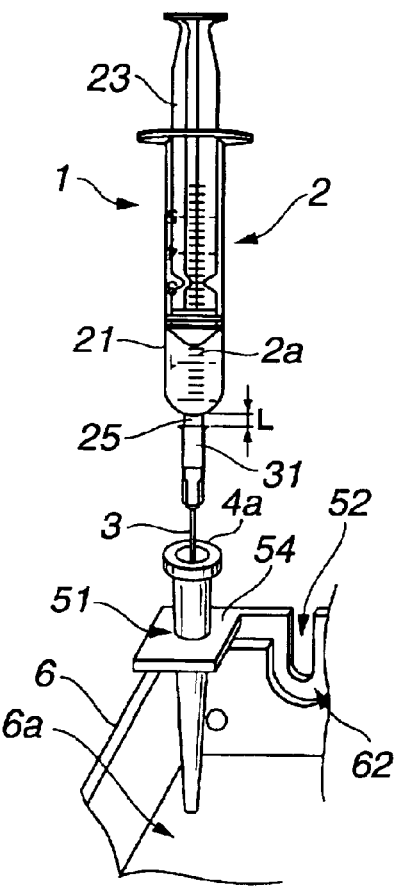
FIG. 5B is a view showing a state in which a needle is inserted into the cap.

Next, chemicals are drawn into the outer barrel 21 of the disposable syringe device 1. Then, the needle 3 of the disposable syringe device 1 is stuck into the patient, and the chemicals are injected into the patient. On the completion of the injection of the chemicals, the extreme end of the needle 3 is inserted into the inner hole of the cap 4 standing in the hole 51 as shown in FIG. 5B to prevent the used needle 3 from being left in an exposed state.

Figure 5C:
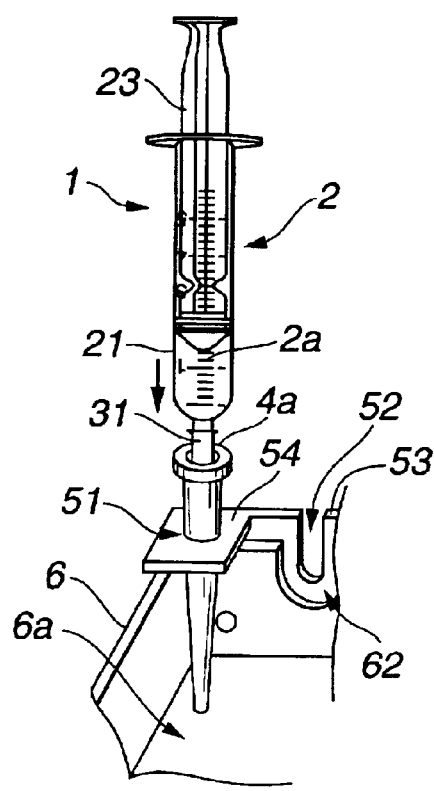
FIG. 5C is a view showing a state in which the cap is attached to the needle again.

Then, the disposable syringe 2 is further forcibly inserted into the cap 4 vertically downward as shown by an arrow in FIG. 5C while keeping the outer peripheral surface of the joint section 31 of the needle 3, which projects from the disposable syringe 2, in contact with the inner peripheral surface of the cap 4. With this operation, the joint section 31 is reliably inserted into and disposed in the cap 4.

That is, the used needle 3 can be covered with the cap 4 again with outer barrel 21 gripped with one hand without the need of directly gripping the cap with a hand or fingers, because when the cap 4 was detached, it was caused to stand in the hole 51 of the syringe auxiliary unit 5A.

Thereafter, a job is performed to extract the used disposable syringe device 1 the needle 3 of which is covered with the cap 4 from the hole 51 and to separate the needle 3 from the disposable syringe 2.

Figure 6A:
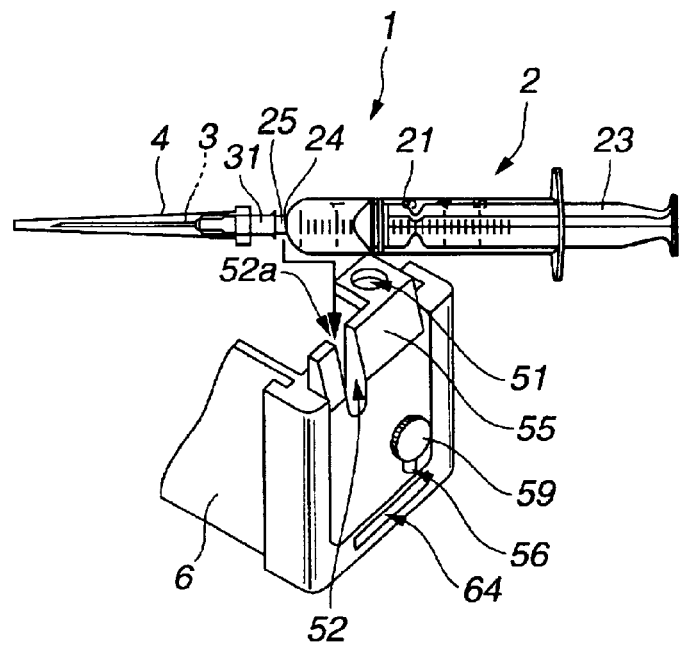
FIG. 6A is a view showing the projection of the outer barrel, where the needle to which the cap is attached again is disposed, faces the opening of a separation/guide groove.

At this time, first, the portion of the projection 25 of the used disposable syringe device 1, which corresponds to the interval having the size "L", is caused to face the opening 52a of the separation/guide groove 52 as shown in FIG. 6A; the portion of the projection 25 is disposed in the separation/guide groove 52 as shown by an arrow in FIG. 6A; and then the disposable syringe device 1 is moved toward the bottom 52b as a whole with the extreme end surface 24 of the outer barrel 21 being in contact with the slanting surface 55 of the syringe auxiliary unit 5A.

With this movement, the base end surface of the joint section 31 of the needle 3 comes into contact with the inner surface of the sheet member 53. When the disposable syringe device 1 is further moved toward the bottom 52b, as shown in FIG. 6B, the interval formed between the base end surface of the joint section 31 and the extreme end surface 24 of the outer barrel 21 is increased so as to separate the joint section 31 from the outer barrel 21.

Figure 6B:
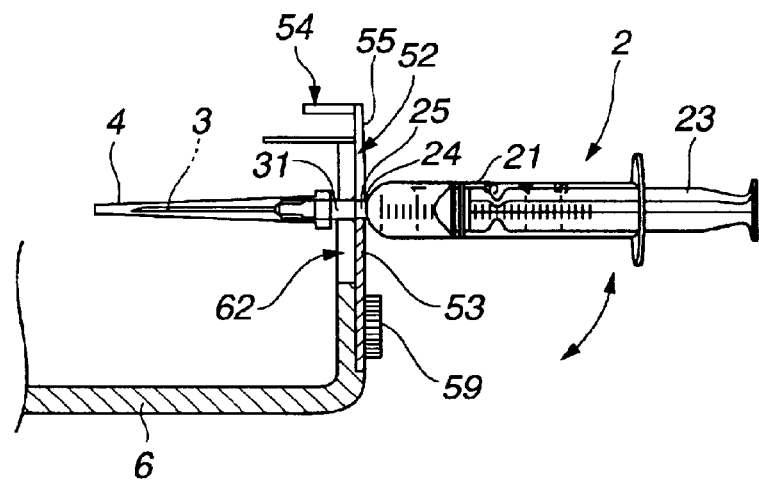
FIG. 6B is a view showing a state in which the projection is moved from the opening of the separation/guide groove to the bottom thereof.
Figure 6C:
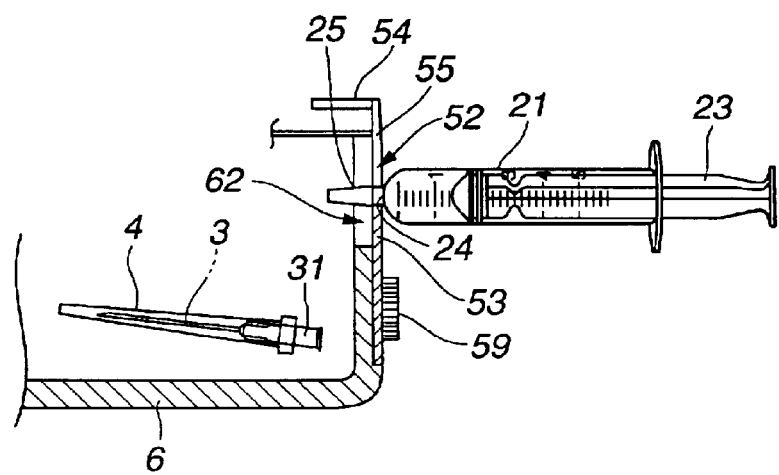

When the projection 25 reaches the vicinity of the bottom 52b, as shown in FIG. 6C, the needle 3 covered with the cap 4 is separated from the projection 25 of the outer barrel 21 and falls toward the bottom 6a of the needle accommodation box 6. In contrast, only the disposable syringe 2 is left at hand and discarded into a waste bag previously prepared in the visiting car.

Note that when the needle 3 is not yet separated from the projection 25 at the time the projection 25 reaches the vicinity of the bottom 52b as shown in FIG. 6B, a swing operation, for example, is applied to the disposable syringe device 1 at hand as shown by an arrow in FIG. 6B. Thus, the needle 3 is separated from the projection 25 of the outer barrel 21, and the needle 3 covered with the cap 4 falls into the needle accommodation box 6 as shown in FIG. 6C.

With this operation, the needle 3, which is covered with the cap 4 and will be accommodated in a piercing-resistant vessel later, is accommodated in the bottom 6a of the needle accommodation box 6. In contrast, the disposable syringe 2, which can be discarded into a dedicated carton case, is accommodated in a waste bag. With this operation, the separation of the needle 3 from the disposable syringe 2 is completed.

As described above, when the disposable syringe device is used, the cap, which covers the needle provided with the disposable syringe, is disposed and held in the hole of the syringe auxiliary unit, which reliably prevents the cap from being lost when an injection is made to a patient.

Further, when the used needle is covered with the cap again after the injection is made to the patient, a doctor or a nurse can attach the cap to the needle again by gripping the disposable syringe with one hand without the need of gripping the cap with the other hand, that is, by inserting the needle into the inner hole of the cap standing in the hole with the one hand.

With these operations, the occurrence of a medical disaster that is caused by a needle stuck in a hand or a finger during a medical treatment can be prevented.

Further, when the portion of the projection of the outer barrel, which corresponds to the above interval, is disposed to the opening side of separation/guide groove and the disposable syringe device is moved in the bottom direction, the needle, which is covered with the cap, of the used disposable syringe device can be separated from the projection of the outer barrel with one hand.

With this operation, the needle, which is covered with the cap and is to be accommodated in the piercing-resistant vessel, can be easily and reliably segregated from the disposable syringe, which can be discarded into the dedicated carton box. At the same time, the occurrence of a medical disaster that the needle is stuck in a hand or a finger can be prevented.

Further, the syringe auxiliary unit can be replaced, disinfected, and sterilized, when necessary, because it can be removed from the needle accommodation box.

Note that the first embodiment shows the arrangement that the syringe auxiliary unit is integrated with the needle accommodation box that is fixed to the visiting car. However, the needle accommodation box integrated with the syringe auxiliary unit may be fixed on a cart disposed in an operating room or on a treatment table in a clinic.

In particular, when the needle accommodation box integrated with the syringe auxiliary unit is fixed on the cart disposed in the operating room, the cap can be reliably prevented from being lost, even if it is necessary to frequently attach and detach the cap to and from the needle. Further, the occurrence of a medical disaster that a hand or a finger is stuck with the needle in a job for covering the needle with the cap, can be reliably prevented.

Further, a disposable sheet-like member, for example, may be detachably disposed in the needle accommodation box 6. With this arrangement, when the needle 3 integrated with the cap 4 is moved from the needle accommodation box 6 to the piercing-resistant vessel, the needle 3 integrated with the cap 4 can be taken out together with the sheet-like member by taking out the sheet-like member from the needle accommodation box 6.

Further, in the first embodiment, the needle 3 covered with the cap 4 is separated from the projection 25 of the outer barrel 21 during the doctor's round visit. However, the used needle 3 covered with the cap 4 may be temporarily discarded into the waste bag in a state that it is integrated with the disposable syringe 2, and the needle 3 covered with the cap 4 may be separated from the projection 25 of the outer barrel 21 after the doctor's round visit.

Figure 7A:
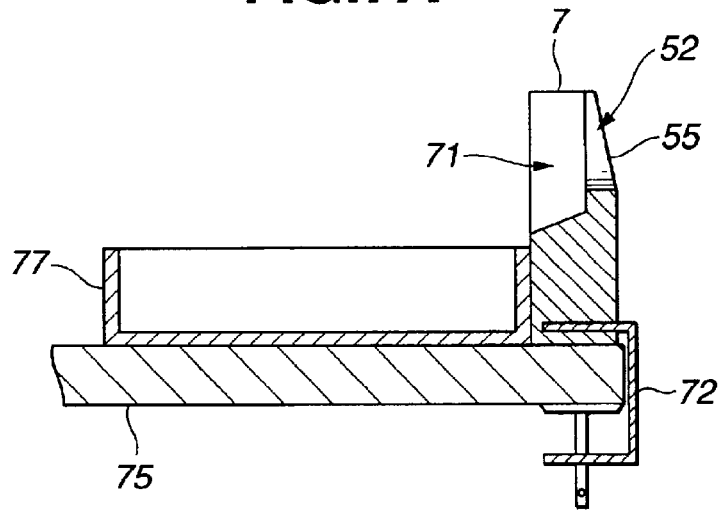
FIG. 7A is a view explaining an example of the arrangement of a needle separator as a modification of the separation/guide groove.

In this case, for example, a needle separator 7 acting as a syringe auxiliary unit, which is provided only with the separation/guide groove 52 and an escape groove 71, is disposed on a working table 75 integrally therewith through a fixture 72, and a box 77 is disposed in the vicinity of the needle separator 7 as shown in FIG. 7A. Then, a job for separating the needle 3 to which the cap 4 is attached again from the disposable syringe 2 may be performed in this state.

Figure 7B:
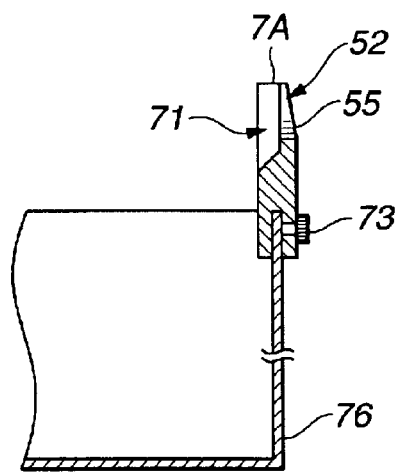
FIG. 7B is a view explaining another example of the arrangement of the needle separator.

Further, as shown in FIG. 7B, a needle separator 7A may be directly attached to, for example, a pail 76 acting as the piercing-resistant vessel through a fixing screw 73. Then, the job for separating the needle 3 to which the cap 4 is attached again from the disposable syringe 2 may be performed in this state.

With this arrangement, a job for separating the needle, which is covered with the cap, of the used disposable syringe device from the projection of the outer barrel can be performed with one hand. Accordingly, the occurrence of a medical disaster that a hand or a finger is stuck with the needle during the job for separating the needle from the disposable syringe can be prevented.

A second embodiment of the present invention will be described below with reference to FIGS. 8 to 11.

Figure 8:
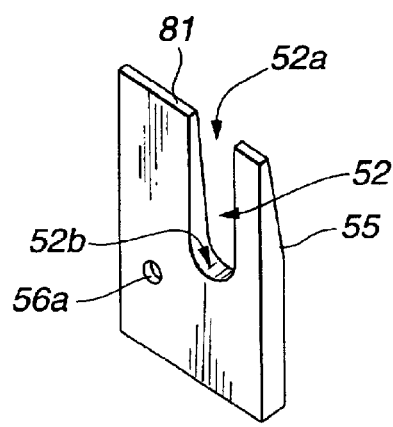

In the second embodiment, a needle separation auxiliary unit 81, which is composed of a separation/guide groove 52 acting as a needle separating section and a slanting surface 55, is arranged as a type of syringe auxiliary units as shown in FIG. 8, in place of the syringe auxiliary unit 5A of the first embodiment in which the cap holding section is integrated with the needle separating section. Further, a cap holding auxiliary unit 82 acting as a type of the syringe auxiliary units is arranged such that it is provided with a plurality of cap clamping/holding sections 83a acting as a cap holding unit as shown in FIG. 9A.

Figure 10:
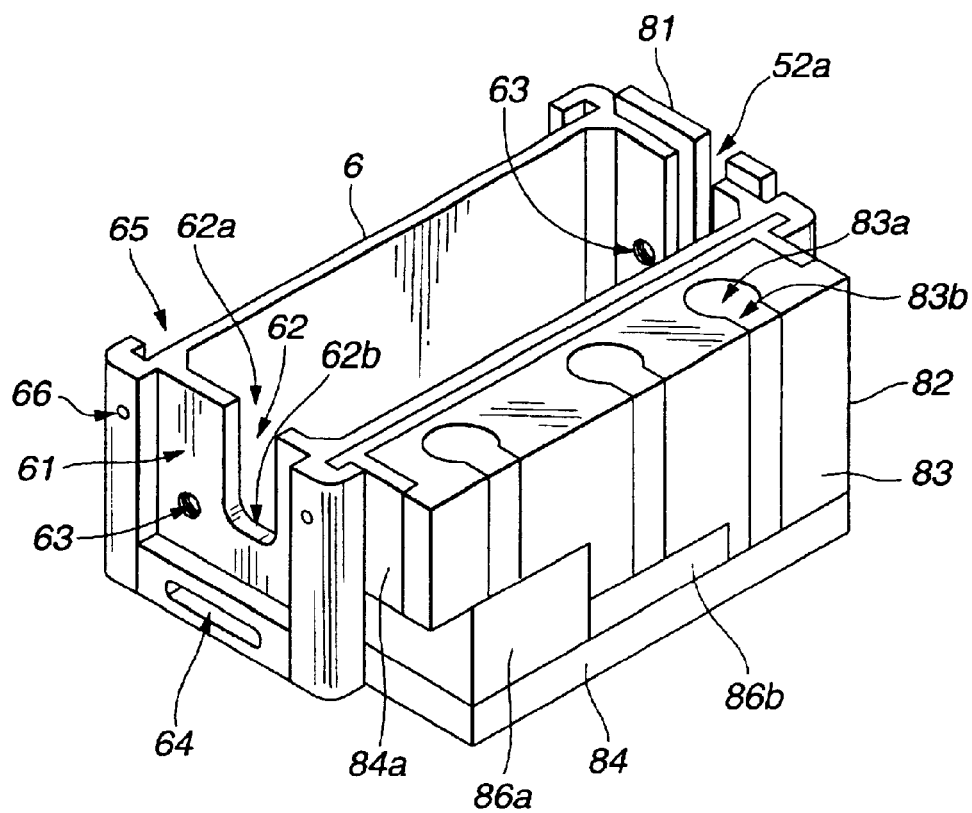

Then, as shown in FIG. 10, a syringe barrel/needle hold/separation unit is arranged by mounting the needle separation auxiliary unit 81 and the cap holding auxiliary unit 82 on first and second auxiliary unit mounting sections 61 and 65 of the needle accommodation box 6, respectively.

Figure 9A:
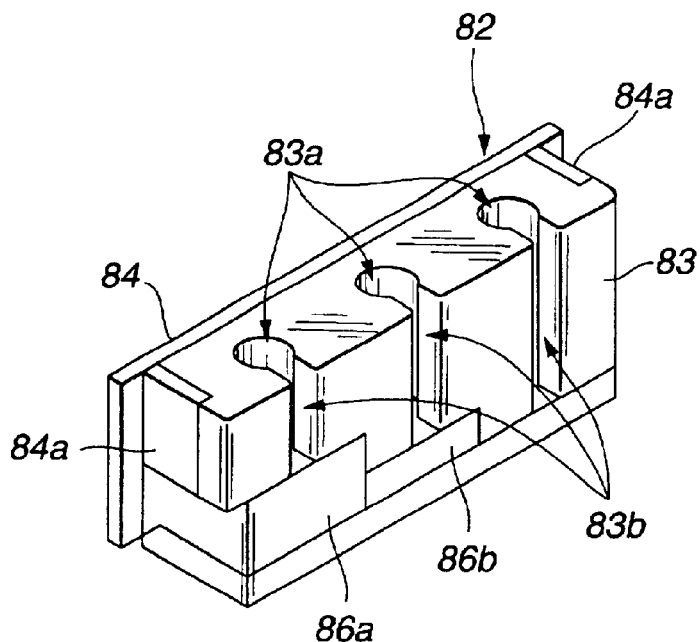
FIG. 9A is a perspective view of a cap holding auxiliary unit.
Figure 9B:
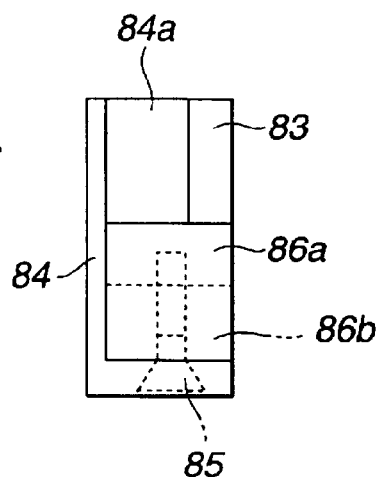
FIG. 9B is a side elevational view of the cap holding auxiliary unit.

As shown in FIGS. 9A and 9B, the cap holding auxiliary unit 82 is composed of an auxiliary unit main body 84, cap length adjustment members 86a and 86b which are integrated together by, for example, countersink screws 85, and an elastic block 83 clamped between a pair of elastic member holding sections 84a.

The auxiliary unit main body 84 is formed in an approximately L-shaped cross section, and the pair of elastic member holding sections 84a project therefrom. The cap length adjustment members 86a and 86b, which act as a cap length adjusting section, are formed in thicknesses corresponding to cap lengths and fixed on the bottom of the auxiliary unit main body 84. The elastic block 83 is an elastic member which has a predetermined elastic force and is composed of, for example, an urethane resin formed in a predetermined shape.

The elastic block 83 is provided with steps so that it is formed in thicknesses corresponding to, for example, three types of the caps 4 each having a different length. The elastic block 83 has the cap clamping/holding sections 83a and cap taking-out grooves 83b each formed at a predetermined position, and the cap taking-out grooves 83b communicate with the cap clamping/holding sections 83a. The cap taking-out grooves 83b are narrower than the cap clamping/holding sections 83a.

As shown in FIG. 10, the needle separation auxiliary unit 81 is fixed to the auxiliary unit mounting section 61 of the needle accommodation box 6 integrally therewith through the fixing screw 59. Further, the auxiliary unit main body 84 is fixed to the second auxiliary unit mounting sections 65 integrally therewith by disposing the fixing screws (not shown) in the second female screw sections 66. The elastic block 83 and the cap length adjustment members 86a and 86b are disposed to the auxiliary unit main body 84 integrally therewith. That is, the cap holding auxiliary unit 82 is fixed to the second auxiliary unit mounting section 65.

Then, the needle accommodation box 6 integrated with the auxiliary units 81 and 82 is fixed to the visiting car integrally therewith at a predetermined position through the fixture (not shown), and a doctor's round visit is performed.

When it is necessary to inject chemicals to a patient during the doctor's round visit, first, a disposable syringe device 1 carried by the visiting car is taken out. Then, the cap 4 of the disposable syringe device 1 is detached. At this time, the cap 4 is pushed into a cap clamping/holding section 83a corresponding to the length of the cap 4 from thereabove.

Figure 11:
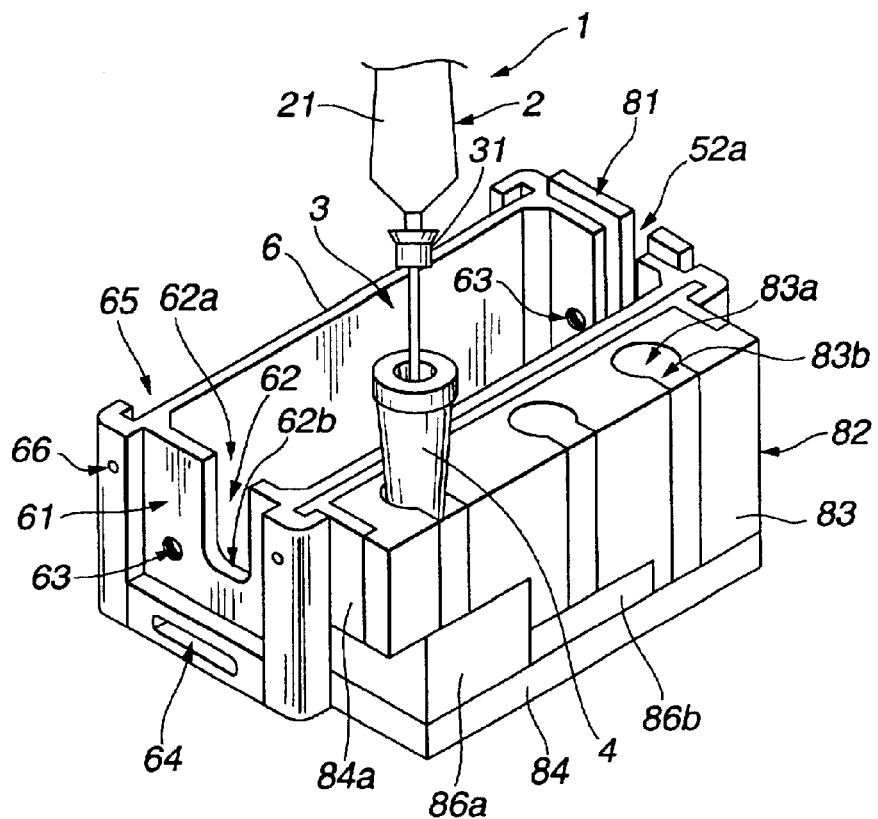

Then, a mid-portion of the slanting surface of the cap 4 is inserted and held under pressure by the elastic force of the elastic block 83 in a state that the extreme end surface of the cap 4 comes into the cap length adjustment member 86a as shown in FIG. 11. The cap 4 stands approximately upright when it is inserted and held under pressure.

After the needle 3 of the disposable syringe device 1 is used, the extreme end of the needle 3 is inserted into the inner hole of the cap 4 standing in the cap clamping/holding section 83a to prevent the used needle 3 from being left exposed.

Then, the disposable syringe 2 is forcibly pushed. With this operation, the joint section 31 of the needle 3 is reliably inserted into and disposed in the cap 4. Thereafter, a job is performed in the needle separation auxiliary unit 81 to extract the used disposable syringe device 1 the needle 3 of which is covered with the cap 4 through the cap taking-out groove 83b communicating with the cap clamping/holding section 83a, and to separate the needle 3 from the disposable syringe 2.

As described above, the cap holding auxiliary unit is composed of the auxiliary unit main body 84, the elastic block, which is disposed to the auxiliary unit main body and includes the plurality of cap clamping/holding sections, and the cap length adjustment members threaded with and fixed to the auxiliary unit main body in the state that they are integrated together. Accordingly, even if disposable syringe devices the caps thereof have a different length are carried by the visiting car, the caps can be held by the cap clamping/holding sections 83a, which corresponding to the lengths thereof, in a stably standing state.

Further, when the needle is forcibly pushed into the cap, the extreme end surface of the cap is pushed against the cap length adjustment member so as to permit the cap to be reliably attached to the needle because the cap is inserted and held under pressure making use of the elastic force of the elastic block 83. The other operations and advantages of the second embodiment are similar to those of the first embodiment.

Note that reference numeral 56a shown in FIG. 8 denotes an escape hole through which the screw portion of the fixing screw 59 passes.

Further, only the needle separation auxiliary unit 81 or the cap holding auxiliary unit 82 may be integrated with the needle accommodation box.

Figure 12A:
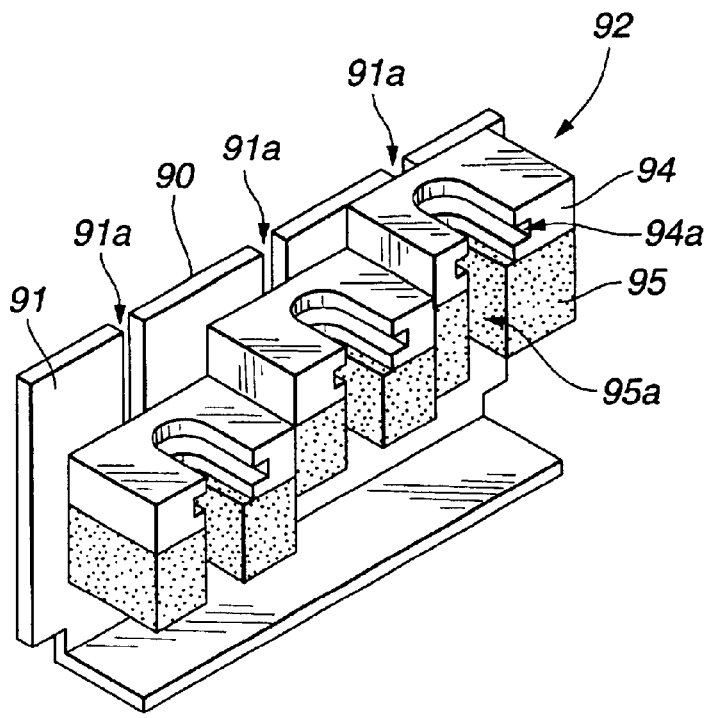
FIG. 12A is a perspective view showing another example of the arrangement of the cap holding auxiliary unit.
Figure 12B:
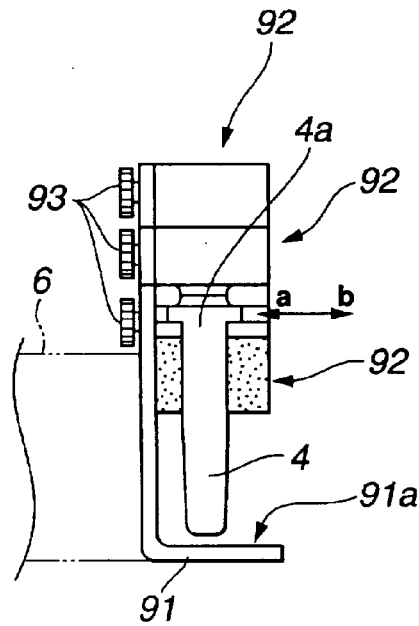
FIG. 12B is a view explaining the another example of the arrangement of the cap holding auxiliary unit.

Further, the cap holding auxiliary unit 82 disposed to the second auxiliary unit mounting sections 65 is not limited to the arrangement in which the auxiliary unit main body 84, the elastic block 83, and the cap length adjustment members 86a and 86b are integrated together, and may be arranged as, for example, a cap holding auxiliary unit 90 as shown in FIGS. 12A and 12B. The cap holding auxiliary unit 90 is arranged such that cap holding blocks 92, which advance and retract freely, are disposed in cap length adjustment grooves 91a formed in a holding unit main body 91 through a plurality of fixing screws 93.

As shown in the figure, the cap holding block 92 is composed of cap locking blocks 94 and elastic block members 95 disposed thereunder and having holding grooves 95a formed therein.

Each of the cap locking blocks 94 has a collar disposition groove 94a formed therein with which the collar section 4a of the cap 4 is loosely engaged. Further, each of the holding grooves 95a clamps and holds a portion of the collar section 4a in the vicinity of the lower end thereof with a predetermined elastic force.

In the second embodiment, when it is necessary to inject chemicals to the patient during the doctor's round visit, the disposable syringe device 1 carried by the visiting car is taken out. Thereafter, the collar section 4a of the cap 4 that is fitted on the needle 3 is disposed in a collar disposing groove 94a at an inner predetermined position against the elastic force of a holding groove 95a as shown in an arrow a of FIG. 12B without removing the cap 4 from the disposable syringe device 1.

With this operation, the cap 4 is inserted into the predetermined position of the cap holding auxiliary unit 90 under pressure by the elastic force of the holding groove 95a formed to the elastic block member 95 and held thereat without causing the extreme end surface of the cap 4 to be in contact with a lower surface 91b of the holding unit main body 91.

When the disposable syringe 2 is moved upward in this state, the opening side surface of the collar section 4a comes into contact with the collar disposing groove 94a, and thereby the cap 4 can be detached from the disposable syringe 2 while leaving only the cap 4 in the cap holding auxiliary unit 90.

In contrast, after the disposable syringe device 1 is used, the extreme end of the used needle 3 of the disposable syringe device 1 is caused to face the inner hole of the cap 4 locked to the collar disposing groove 94a and inserted thereinto to prevent the used needle 3 from being left in an exposed state. Finally, the disposable syringe 2 is forcibly pushed. At this time, the extreme end side surface of the collar section 4a comes into contact with the collar disposing groove 94a, and thereby the joint section 31 of the used needle 3 is reliably inserted into the cap 4 and disposed therein.

Thereafter, the collar section 4a of the used disposable syringe device 1 having the needle 3 covered with the cap 4 is extracted from the collar disposing groove 94a against the elastic force of the holding grooves 95a as shown by an arrow b of FIG. 12B.

As described above, the cap holding block is formed to freely move with respect to the cap length adjustment grooves formed in the holding unit main body as well as the collar disposing grooves are formed in the cap locking blocks that constitute the cap holding block. Accordingly, it is possible to adjust the heights of the collar disposing grooves from the lower surface of the holding unit main body according to the lengths of caps, and to easily attach and detach the caps to and from the needles by locking the collar sections of the caps to the collar disposing grooves.

Further, in the second embodiment, when the heights of the collar disposing grooves from the lower surface of holding unit main body are adjusted, the collar section of caps are locked by the collar disposing grooves. Thus, the heights can be easily adjusted without the need of abutting the extreme ends of the caps against the lower surface.

Note that while the above embodiments show the arrangement that the cap stands approximately upright, an arrangement that the cap stands obliquely may be also employed.

Further, while the disposable syringe device 1 of the above embodiments is arranged such that the needle 3 is fixed by being fitted over the projection 25 of the outer barrel 21, the disposable syringe device 1 may be also arranged as the locking type disposable syringe device 1A as shown in FIG. 1B. When the locking type disposable syringe device 1A is used, a needle covered with a cap is separated from a disposable syringe manually, while the cap is detached from and attached again to the needle in the same way as that of the aforementioned embodiments.

Further, the cap holding auxiliary units 82 and 90 may be integrated with a metal vessel carried by the work table and the visiting car through a fixture (not shown) provided with the cap holding auxiliary units 82 and 90 so that a cap is held thereby.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A disposable syringe device auxiliary unit for preventing iatrogenic infection through a needle, comprising:
    a cap holding section for disposing and holding therein a cap which covers, when a medical treatment is performed, a needle positioned at the extreme end of a syringe barrel constituting a disposable syringe device, the cap having a cap length measured from a collar section of the cap to the opposite extreme end of the cap;
    a plurality of members formed in thicknesses corresponding to different cap lengths, and being fixed on an extreme end portion of the cap holding section; and
    a needle separating section for separating the needle, which is covered with the cap and fitted on an end of the syringe barrel, from the syringe barrel,
    wherein the cap holding section has bottom portions defined by the plurality of members.

2. A disposable syringe device auxiliary unit according to claim 1, wherein the needle separating section comprises a syringe guide section for guiding the disposable syringe device to a predetermined position, and a slanting surface having a predetermined angle is formed on the syringe guide section.

3. A disposable syringe device auxiliary unit according to claim 1, wherein the cap holding section is integrated with the needle separating section.

4. A disposable syringe device auxiliary unit according to claim 2, wherein the cap holding section is integrated with the needle separating section.

5. A disposable syringe device auxiliary unit according to claim 1, wherein the cap holding section comprises a cap locking section.

6. A disposable syringe device auxiliary unit for preventing iatrogenic infection infecting through a needle, comprising:
    a cap holding section for disposing and holding therein a cap which covered, when a medical treatment was performed, a needle positioned at the extreme end of a syringe barrel constituting a disposable syringe device, the cap having a cap length measured from a collar section of the cap to the opposite extreme end of the cap; and
    a plurality of members formed in thicknesses corresponding to different cap lengths, and being fixed on an extreme end portion of the cap holding section,
    wherein the cap holding section has bottom portions defined by the plurality of members.

7. A disposable syringe device auxiliary unit for preventing iatrogenic infection infecting through a needle, comprising:
    a needle separating section for separating the needle, which is covered with a cap and fitted on an end of the syringe barrel, from the syringe barrel, the cap having a cap length measured from a collar section of the cap to the opposite extreme end of the cap;
    a cap holding section; and
    a plurality of members formed in thicknesses corresponding to different cap lengths, and being fixed on an extreme end portion of the cap holding section,
    wherein the cap holding section has bottom portions defined by the plurality of members.

8. A disposable syringe device auxiliary unit according to claim 1, further comprising a needle accommodation box having auxiliary unit mounting sections on which at least one of the cap holding section and the needle separating section is mounted.

9. A disposable syringe device auxiliary unit according to claim 6, further comprising a needle accommodation box having auxiliary unit mounting sections on which the cap holding section is mounted.

10. A disposable syringe device auxiliary unit according to claim 7, further comprising a needle accommodation box having auxiliary unit mounting sections on which the needle separating section is mounted.

* * * * *